United States Patent [19]
Schildmeyer et al.

[11] Patent Number: 5,872,622
[45] Date of Patent: Feb. 16, 1999

[54] CONDENSATION NUCLEUS COUNTER HAVING VAPOR STABILIZATION AND WORKING FLUID RECOVERY

[75] Inventors: Frederic C. Schildmeyer; Brian J. Shahan, both of Grants Pass, Oreg.

[73] Assignee: Met One, Inc., Grants Pass, Oreg.

[21] Appl. No.: 888,736

[22] Filed: Jul. 7, 1997

Related U.S. Application Data

[63] Continuation-in-part of Ser. No. 695,658, Aug. 12, 1996, Pat. No. 5,675,405.
[51] Int. Cl.⁶ .................................................. G01N 15/06
[52] U.S. Cl. ............................................. 356/37; 356/339
[58] Field of Search .............................. 356/37, 336, 338, 356/339

[56] References Cited

U.S. PATENT DOCUMENTS

| | | | |
|---|---|---|---|
| 3,462,609 | 8/1969 | Beattie | 356/37 |
| 4,293,217 | 10/1981 | Bird et al. | 356/37 |
| 4,449,816 | 5/1984 | Kohsaka et al. | 356/37 |
| 4,790,650 | 12/1988 | Keady | 356/37 |
| 4,950,073 | 8/1990 | Sommer | 356/37 |
| 4,967,187 | 10/1990 | Dumas et al. | 356/37 |
| 5,026,155 | 6/1991 | Ockovic et al. | 356/37 |
| 5,118,959 | 6/1992 | Caldow et al. | 250/573 |
| 5,239,356 | 8/1993 | Holländer et al. | 356/37 |

Primary Examiner—Richard A. Rosenberger
Attorney, Agent, or Firm—Thomas Schneck; John P. McGuire, Jr.

[57] ABSTRACT

A particle counter of the condensation nucleus type wherein a primary stream of fluent material containing particles enlarged by vapor condensate of a working fluid flow through a viewing volume. A secondary stream of fluent material, termed purge gas, surrounds the primary stream of fluent material as the primary stream traverses the view volume, thereby providing a boundary layer of fluent material, reducing turbulence of the primary stream. The two streams are merged after passing through the view volume and the merged stream is drawn into one or more coalescent filters for conversion of vapor to working fluid which is then recycled for reuse, thereby extending the life of the working fluid and preventing escape of vapor which might contaminate the ambient environment.

19 Claims, 6 Drawing Sheets

CONDENSATION NUCLEUS COUNTER HAVING VAPOR STABILIZATION AND WORKING FLUID RECOVERY

CROSS REFERENCE TO RELATED APPLICATION

This application is a continuation-in-part of prior application Ser. No. 08/695,658 filed Aug. 12, 1996 now U.S. Pat. No. 5,675,405, issued Oct. 7, 1997.

TECHNICAL FIELD

The present invention pertains to the field of airborne particle detection systems and, more particularly, to condensation nucleus counters.

BACKGROUND ART

Condensation nucleus counters (CNCs) provide the optical resolution necessary to detect and count sub-micron size particles by magnifying the size of the particles using condensate. CNCs operate on the principle of a cloud chamber. Vapor obtained by super-saturation of a gas derived from a working fluid, such as glycol, condenses upon sub-micron particles entrained in a sample gas, producing droplets on the order of a micron. In this fashion, the particles to be counted function as condensation nuclei for the vapor. The droplets, still entrained as sample gas, pass into a view volume of a particle counter operating according to light extinction or scattering principles. The droplets attenuate or scatter light in a beam of the particle counter, resulting in an appropriate output signal relative to particle condensation. The accuracy is dependent on the thermal and signal processing thresholds. The stream of fluent material, which includes droplets, passes through the optical beam, initiating the signal pulse. This flow region or view volume is defined by the optical and flow parameters of the detection system. Thus, some view volume characteristics can be controlled through nozzle and port design.

U.S. Pat. No. 5,118,959 to Caldow et al. discloses a CNC with a porous saturation below a condenser. An optical block containing a viewing volume is located above the condenser.

U.S. Pat. No. 5,239,356 to Hollander et al. discloses a condensation nucleus counter including a humidifier zone, a condensation zone extending orthogonally thereto and an optical detection system. The humidifying zone includes a duct and a hollow space extending parallel to the duct, but separated therefrom by a permeable material. A vaporizable liquid is received within the hollow space. The condensation zone includes a duct and a hollow space extending parallel thereto. Separating the duct from the hollow space is a permeable material. Particulate matter, entrained in sample air, is guided into the duct of the humidifying zone, where it is saturated. Upon passing through the condensation zone, the saturated air is supersaturated and condenses around the particulates.

U.S. Pat. No. 5,026,155 to Ockovic et al. discloses a process for sizing particles using condensation nucleus counting. The process employs a standard condensation nucleus counter in which the condensing temperature of a saturated working fluid is incrementally adjusted. In this manner, the sensitivity of the counter may be adjusted to afford discrimination of particles entrained in a gas, according to size.

U.S. Pat. No. 4,950,073 to Sommer discloses a submicron particle counter for counting particles entrained in air which includes a saturator, a condenser and an optical detector. Conduits extend through a bath of liquid contained in the saturator so that sample streams passing therethrough are heated by the bath. A flow divider separates the sample stream into a plurality of laminar flow streams, corresponding to the number of conduits in the bath. The condenser is a heat exchanger having a plurality of tubes with funnel-shaped inlet ends. The inlet ends are positioned over the bath of the saturator, with the tubes being inclined toward their inlet ends so that condensed vapor flows back into the bath.

U.S. Pat. No. 4,790,650 to Keady discloses a condensation nucleus counter including an inlet orifice leading to a flow path within a saturator. A condenser is in fluid communication with the saturator. Particulates entrained in a gas flow passing through the saturator have condensation accumulated thereon, forming a plurality of droplets. The plurality of droplets pass through an optical counter.

U.S. Pat. No. 4,449,816 to Kohsaka et al. discloses a system and a method of measuring hyperfine particles including a mixing chamber in fluid communication with both a saturated vapor chamber and a high temperature vapor chamber. An aerosol inlet is in constant fluid communication with the high temperature vapor chamber. The inlet is also in selective fluid communication with the saturated vapor chamber via a valve. An air aerosol containing fine particles is led into both the saturated vapor chamber and the high temperature vapor chamber, respectively, to produce saturated vapor aerosols. The two saturated vapor aerosols are led into the mixing chamber so that the aforementioned vapor is condensed on the aerosol particles. A particle detection station is included to measure the aerosol particles.

A problem encountered in prior art CNC devices is that vapor flow is carefully regulated until the flow enters the viewing volume. At this point, flow characteristics are largely neglected. However, view volume dynamics can play a key role in velocity profiling, false count elimination and contamination isolation. Yet turbulence expands the flow stream, removing some particles from view of the optics, and causing recirculation of other particles so that they are counted two or more times.

Another problem encountered in the prior art is that although CNC devices attempt to count small particles with great precision, they introduce vapor and particulate matter in the production environment where they are used. This occurs when vapor from the flow stream is exhausted and now, not only the particles entrapped in the vapor return to the ambient environment, but also the vapor. Where the working fluid in a vapor phase is not water, a new foreign substance is introduced into the ambient environment in small but measurable amounts.

An object of the invention was to devise a condensation nucleus counter having improved vapor flow, especially in the viewing volume, exhaust filtration and working fluid recovery.

SUMMARY OF INVENTION

The above object has been achieved by providing particle counting apparatus of the CNC type with a view volume within an optics block or region having a constricted flow path for the sample gas containing particles enlarged by condensate. Constriction is maintained within the beam trajectory by a boundary layer formed by a second gas, termed a purge gas, which pressurizes the view volume and surrounds the flow stream containing the sample gas, thereby constricting the flow stream. The purge gas is exhausted, together with the sample gas, on an outlet side of the view volume opposite the inlet side. The optics portion of the view volume operates the same as in the past, except that now the flow stream is constricted to be within the beam. Heating of the block defining the view volume prevents condensation of vapor on the block. Thus, there is both flow stabilization and thermal stabilization of enlarged particles within the optics block.

Leaving the optics block, the flow stream is pumped toward filters which remove the liquid component from enlarged particles. A first filter, preferably foam, provides a condensing surface for the cooling vapor liquid phase transition. The fluid leakage of such a filter is directed towards the working fluid reservoir. A second filter, in overflow relation with the first filter, has an absorptive medium, such as activated charcoal, which removes the remaining vapor from the flow stream, allowing leakage to reach the working fluid reservoir. By providing tandem filters in the exhaust path of the flow stream, a percentage of the working fluid is filtered and recycled, minimizing environmental contamination and extending fluid lifetime.

Figure 1:
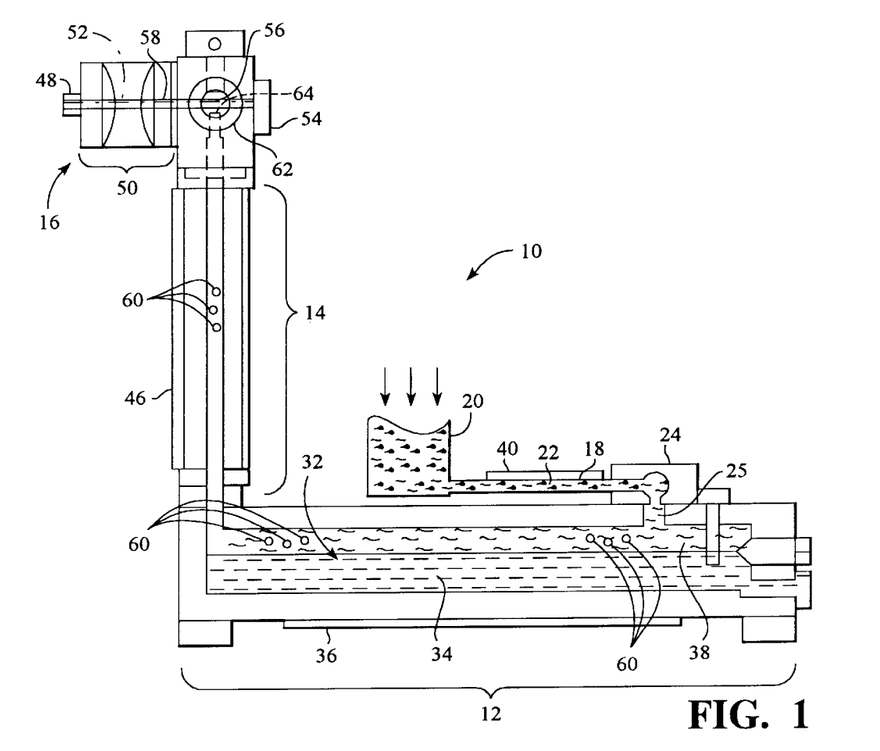
FIG. 1 is a sectional side view of a condensation system for a condensation nucleus counter to be used in the present invention.

BEST MODE FOR CARRYING OUT THE INVENTION (a) Basic Design of Condensation Chamber The basic design for a CNC chamber is taken, relative to the description associated with FIGS. 1–5, from prior application Ser. No. 08/695,658 by F. Schildmeyer et al. With reference to FIG. 1, a condensation nucleus counter 10 includes a saturator 12, a condenser 14, an optical detector 16 and a conduit 18, all of which are in fluid communication with each other. Conduit 18 is coupled to a supply of a sample gas 20 and is adapted to allow a sample gas stream 22 to flow therethrough. Saturator 12 is disposed between condenser 14 and conduit 18, with condenser 14 disposed between detector 16 and saturator 12. A fluid distribution manifold 24 is disposed between conduit 18 and saturator 12, proximate to an inlet 25 of saturator 12.

Figure 2:
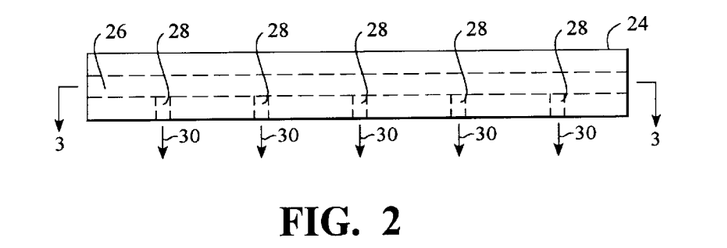
FIG. 2 is a bottom view of a fluid distribution manifold shown in FIG. 1.
Figure 3:
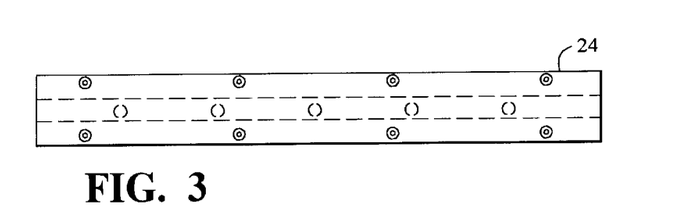
FIG. 3 is a bottom view of the fluid distribution manifold shown in FIG. 2, taken along lines 3—3.
Figure 4:
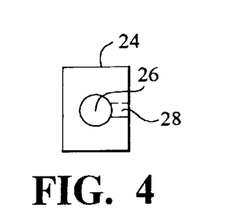
FIG. 4 is an end view of the fluid distribution manifold shown in FIG. 3.

Referring also to FIGS. 2–4, fluid distribution manifold 24 includes a feed chamber 26 and a plurality of channels 28 extending therefrom. Channels 28 are positioned so that sample gas stream 22 entering feed chamber 26 is evenly divided into a plurality of flows 30, with each flow 30 passing through inlet 25 and entering saturator 12.

Saturator 12 defines a saturation chamber 32 that contains a chemical species in a two phase state: liquid 34 and vapor 38. Liquid 34 maintains a reservoir from which the vapor 38 diffuses into the saturator space. Typically, the chemical species is referred to as a vaporizable fluid and comprises of alcohol, preferably glycerol. A first heating system 36 is in thermal contact with saturator 12 to produce the two phase fluid mixture in chamber 32. To ensure efficient thermal transfer between heating system 36 and fluid 34, it is preferred to form saturator from a metal, typically aluminum or an aluminum alloy. Heating system 36 is operated to maintain the temperature of vapor 38 within a predetermined range.

A second heating system 40 is in thermal contact with sample gas stream 22. Second heating system 40 maintains the temperature of flows 30 entering saturator 12 within a predetermined range, with the temperature of vapor 38 maintained above the temperature of flows 30. In this fashion, first 36 and second 40 heating systems function as a temperature control system to maintain a temperature differential between each flow 30, passing through inlet 25, and vapor 38. The aforementioned temperature differential is maintained within a range of 60° to 70° C.

Figure 5:
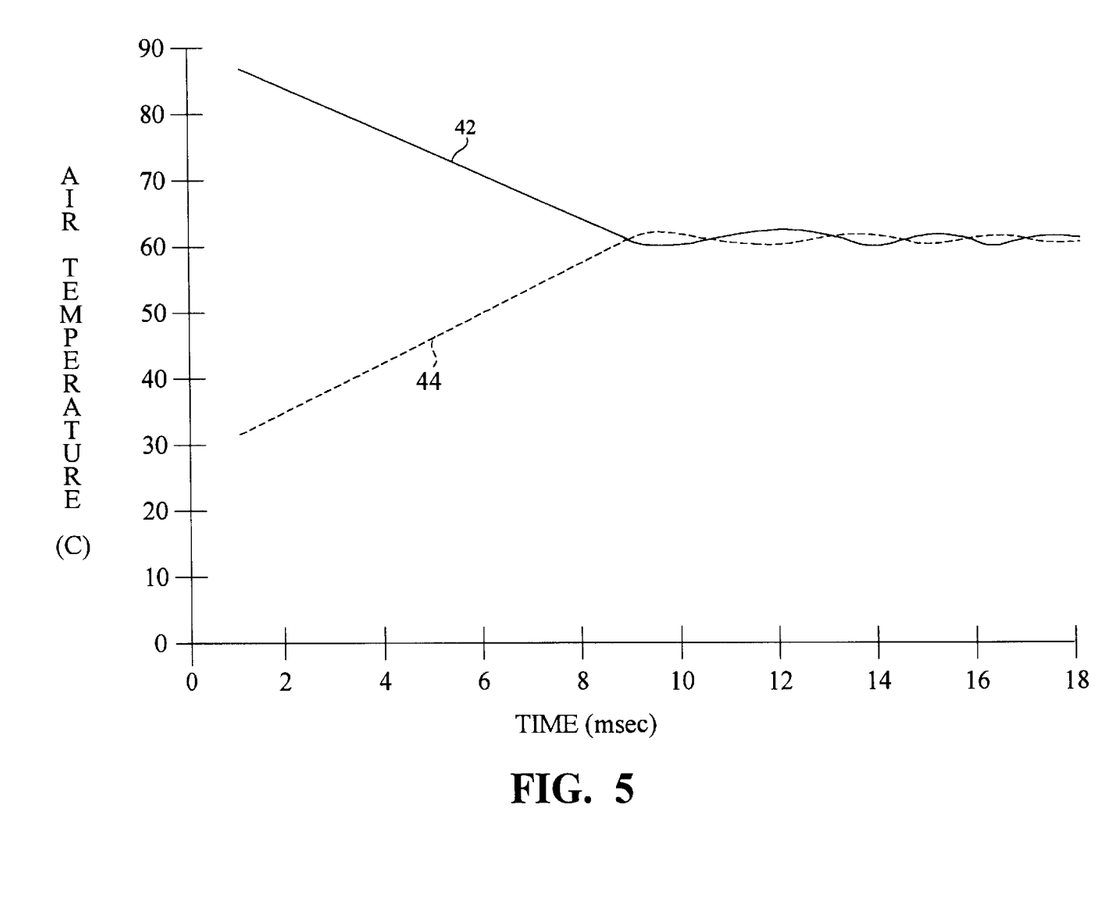
FIG. 5 is a graph showing the thermal transfer between the heated vapor contained in a saturator of the condensation nucleus counter, shown in FIG. 1, and a sample gas stream introduced into the saturator by a fluid distribution manifold shown in FIGS. 2–4.
Figure 6:
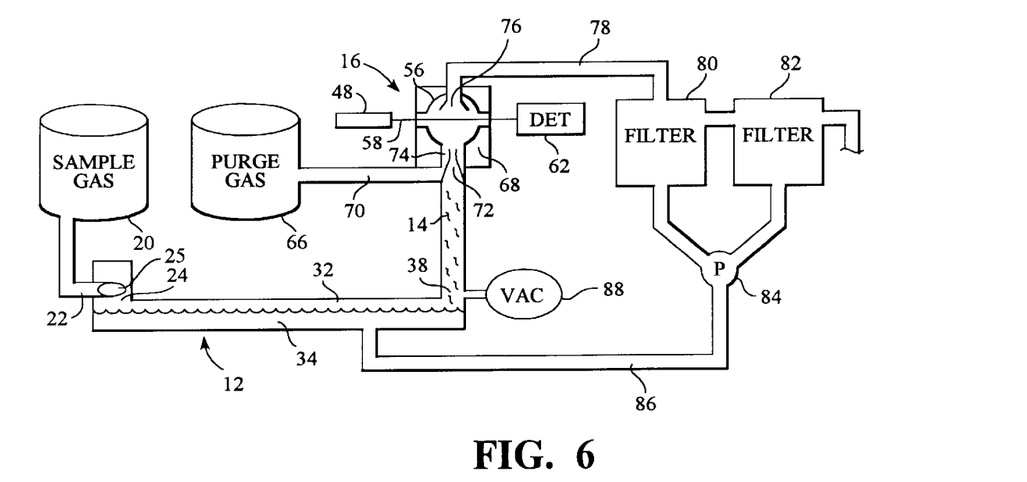
FIG. 6 is a plan view of an entire condensation nucleus counter in accord with the present invention.
Figure 7:
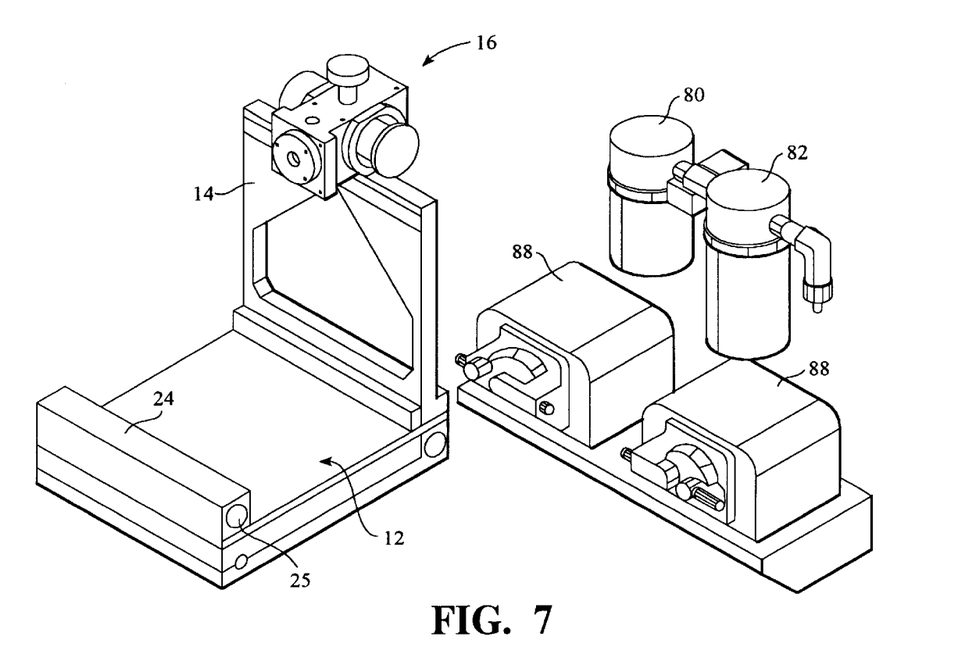
FIG. 7 is an exploded perspective view of a condensation nucleus counter following the plan illustrated in FIG. 6.

Referring also to FIG. 5, it has been found that the temperature differential reduces the entropy associated with vapor 38, positioned proximate to inlet 25. The aforementioned temperature differential creates supersaturation conditions that initiate condensation to form about particulate matter present in flows 30, upon entering saturator 12. Specifically, both the positional and thermal disorder, present in vapor 38, diminishes by interaction with flows 30. The rapid cooling of vapor 38 by flows 30 causes supersaturation of the same. As shown by graphs 42 and 44, vapor 38, shown as a solid line, cools approximately 30° C. within 10 msec. Simultaneously, flows 30, shown as a dashed line, warms approximately 30° C. in the same time, thereby undergoing an increase in entropy. The transforming thermal states begin stabilizing through thin-film formation of vapor 38 onto the surfaces of particulate matter positioned proximate to inlet 25, thereby initiating condensation. By initiating droplet growth in saturator 12, the resolution of counter 10, for a given length of flow path, is greatly increased, because the droplet growth on particulate matter entering condenser 14 has already initiated. Thus, counter 10 affords a higher resolution counter for a given length of flow path and a given flow rate.

To stabilize and facilitate droplet growth, the atmosphere of condenser 14 is maintained at a temperature which is lower than the temperature of vapor 38. To that end, a third heating system 46 is in thermal communication with condenser 14. It is preferred that the temperature of the condenser 14's atmosphere is heated to exceed the temperature of sample gas stream 22 and, therefore, exceed the temperature of the ambient environment that surrounds counter 10. By heating condenser 14's atmosphere and the sample gas stream 22 to exceed the temperature of the environment surrounding counter 10, greater temperature stability is achieved. It was recognized that by employing only heating systems to induce and maintain heterogenous condensation, cooling techniques could be abrogated. Cooling techniques of the prior art lend themselves to support systems (liquid or air cooling), greater cost (component complexity) and reliability problems (thermoelectric cooler failure) which exacerbates problems with controlling the size of droplets produced. By heating condenser 14's atmosphere, the droplet size grown may be effectively controlled, as discussed below.

Typically, detector 16 includes a light source 48 optically coupled to a lens assembly 50, which defines an optical axis 52. Disposed coaxially on optical axis 52, opposite to light source 48, is a light trap 54. Lying along optical axis 52, between light source 48 and light trap 54, is a view volume 56. Light source 48 directs a beam 58 along optical axis 52 through view volume 56. Droplets 60 present therein cause a portion of beam 58 to scatter from optical axis 52, which is collected by a detector 62. Detector 62 produces electrical signals corresponding to the light detected, which may be digitized and displayed accordingly.

In operation, sample gas stream 22 travels through conduit 18 from supply 22 entering feed chamber 26 of fluid distribution manifold 24. Manifold 24 evenly divides sample gas stream 22 by maintaining a pressure drop gradient through channels 28 forming a plurality of flows 30. Flows 30 enter saturator 12, at approximately identical velocities, through inlet 25. Second heating system 40 increases the temperature of sample gas stream 22 so that the temperature of flows 30 are maintained at a constant temperature of approximately 32° C. ±2° C. First heating system 36 maintains the temperature of vapor 38 in saturation chamber 32 between 90°–100° C. Upon flows 30 entering saturator 12, heterogenous nucleation occurs proximate to inlet 25, with particulates present in flows 30 forming nuclei around which condensation of the gas vapor mixture occurs. Droplets 60 formed from the heterogenous nucleation travel through vapor 38 toward condenser 14, where further growth occurs due to molecular collisions with other vapor molecules from saturation chamber 32.

Droplets 60 move through vapor 38 onto condenser 14. Upon exiting saturator 12, however, droplets have differing sizes due to the supersaturation process. More particularly, as growth in saturator 12 occurs, in part, from molecular collisions, the diffusion rate and collision state are not uniform for all droplets. This results in the final droplet diameter probability convoluting with the thermal state distribution function to form a spread in final droplet diameters. Condenser 14 provides some element of control of the final thermal state distribution and narrows the droplet diameter distribution through evaporation and condensation processes. Specifically, heating system 46 raises condenser 14's atmosphere to a temperature in the range of 55° to 65° C. so that droplets 60 having condensed to a larger spectrum of diameters undergo partial evaporation. Droplets associated with a smaller diameter spectrum continue condensation growth. This process of droplet diameter normalization is dependent on tuning the condenser temperature to the mean temperature of the droplet spectrum that leaves saturator 12. To that end, the temperature of condenser 14's atmosphere is maintained at a temperature in excess of the temperature of the environment in which counter 10 is disposed, thereby facilitating a droplet growth using a heat only control system.

Condenser 14 is a parallel plate design with substantially smooth inner surfaces. The smooth surfaces frustrate formation of large condensation droplets on the inner walls and allows drainage back to saturator 12. This helps avoid false counts, i.e., detection of droplets not formed around particulates, which increases the reliability of counter 10 by ensuring only particulate matter of interest is present in detector 16. False counts may be further reduced by having a heated nozzle 64 disposed so as to place condenser 14 in fluid communication with view volume 56. Preferably, nozzle 64 is heated to a temperature approximately ten degrees hotter than saturator 12. The efficiency is further increased by providing all droplets 60 with substantially the same diameter growth so that particulate matter of interest will be provided with a sufficient cross-section to be sensed by detector 16 when passing through view volume 56.

(b) System Design with Improved Optics Block and Working Fluid Recovery

With reference to FIGS. 6 and 7 a complete CNC system in accord with the present invention is seen. Sample gas 20 is shown to originate in a tank, but more typically is pumped from the ambient environment, such as a production facility where cleanliness of the air is being measured. The sample gas is formed into a primary stream of fluent material which is a sample gas stream 22 entering inlet 25 of saturator 12. The saturator 12 has a reservoir of a working fluid or liquid 34 which is vaporized because the air pressure in saturation chamber 32 is lowered by one or more vacuum pumps 88. The reservoir resembles a tray having a length, typically 12 cm and a width, typically 20 cm. The height is typically 5 cm and 80 percent of the height is occupied by fluid. A typical working fluid is glycol. Fluid flows into the saturation chamber through a fluid distribution manifold 24, spreading the primary stream of fluent material over the width of the fluid reservoir.

A vapor 38 moves upwardly in condenser 14, with the vapor condensing on particles, just as the vapor condenses on particles in the saturation chamber 32. As the primary stream of fluent material containing particles with condensate moves upwardly, the primary stream of fluent material passes through an inlet nozzle 72 of optics block 68. The optics block is a block of solid material having a hollow central region to accommodate the gases pumped into the block and also to form a central view volume through which a beam 58 may be projected. The beam 58 is shown to be transmitted directly from a laser 48 to a detector 62. However, detector 62 is at an angle relative to beam 52 for detecting scattered light. Directly opposite laser 48 is a light trap, not shown, which stops the beam. It is possible to have a detector opposite the light source for measurements of light obscuration by particles, but the preferred method of particle counting is by measuring scattered light.

Surrounding the inlet nozzle 72 is a purge inlet 74 for admitting gas through a purge gas conduit 70 coming from a purge gas supply 66. It is preferable that the purge gas be the same as the sample gas, although this is not necessary. Air may be used as the purge gas to reduce costs. The purge inlet 74 is coaxial with inlet nozzle 72 so that the purge gas forms a secondary stream of fluent material surrounding and constituting the primary stream of fluent material by gas pressure. This provides a boundary layer of fluent material about the primary stream of fluent material as the primary stream passes through the view volume in the center of optics block 68. The boundary layer prevents the primary stream fluent material from diffusing laterally outwardly and from becoming turbulent. It is not necessary that the secondary stream of fluent material flow coaxially with the primary stream of fluent material, although this is a preferred configuration. Merely pressurizing the optics block will provide a boundary layer, although more turbulence will be present than if the primary and secondary streams flow together in approximately the same velocity in a coaxial relationship. The nominal flow rate through the optics block is 30 lpm for both the primary and secondary streams of fluent material. The optics block is preferably heated to prevent condensate on the particles from condensing on the optics block. An outlet conduit 78 receives gas from outlet nozzle 76 containing both the primary and secondary streams of fluent material after the streams have crossed the center of the view volume. The gas in outlet conduit 78 is pumped by pump 84 toward the first filter 80 which contains an internal medium promoting coalescence of the vapor in the filter medium and pumping coalesced liquid into recirculation conduit 86 back toward the reservoir in saturator 12. The first filter 80 accommodates a certain volume of gas, less than the entire flow rate through outlet conduit 78 and so an overflow amount passes to a second filter 82 which also has a medium for promoting coalescence of the vapor in the fluid stream flowing in outlet conduit 78. Further overflow from the second filter 82 in filter outlet 83 may go to yet another filter stage or be vented to the local environment to prevent overload and damage to the system.

Figure 8:
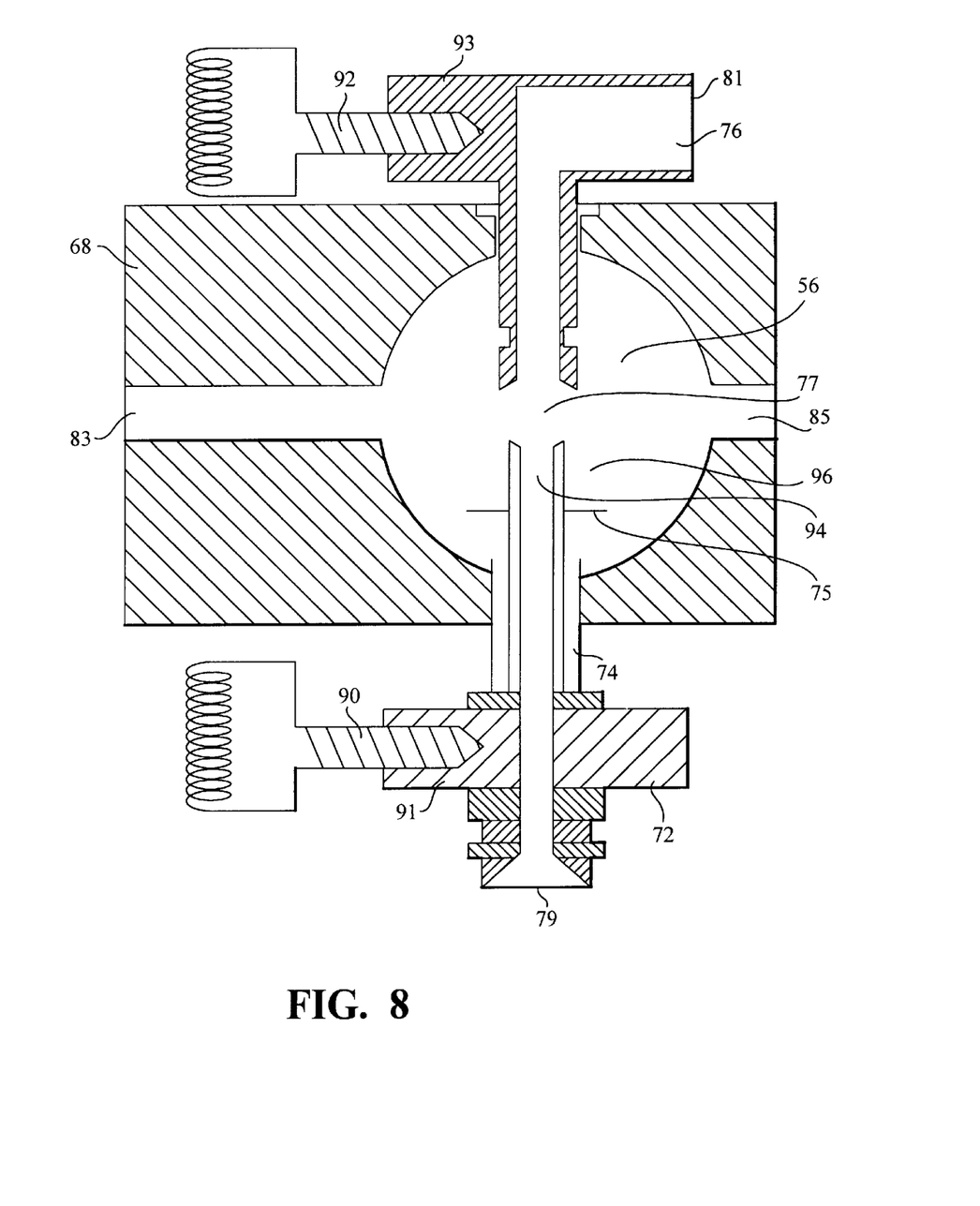
FIG. 8 is a sectional plan view of an optics block with a view volume in accordance with the plan illustrated in FIG. 6.
Figure 9:
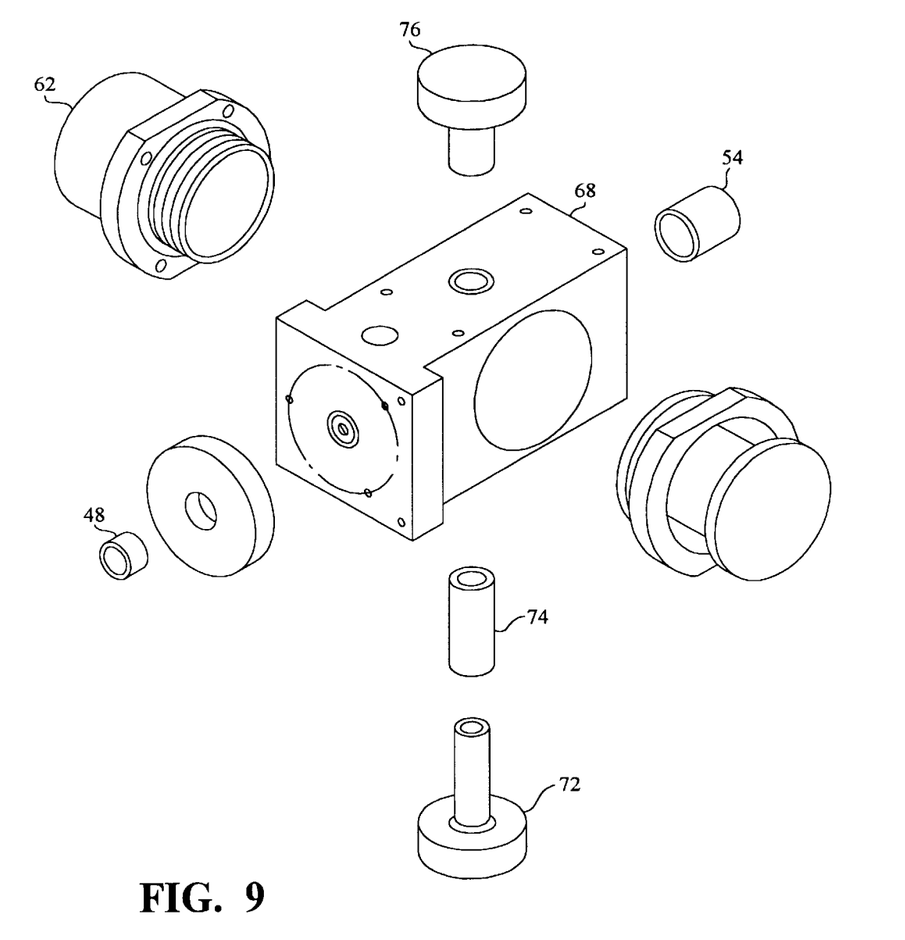
FIG. 9 is an exploded perspective view of an optics block with a view volume following the plan illustrated in FIG. 8.

In FIGS. 8 and 9, optics block 68 is seen to have a central view volume 56. The view volume has a central clear zone 77 between the inlet tip 79 of inlet nozzle 72 and the outlet tip 81 of outlet nozzle 76. The clear zone 77 allows a light beam to pass through the optics block without obstruction using an inlet light channel 83 to communicate with an outlet light channel 85. Actually, there are two outlet light channels, one for a beam stop and another, at an angle to the beam, for sampling light scattered by particles. Not all scattered light is captured, only light at a selected angle, such as 90 degrees to the beam or perhaps a smaller angle.

The primary stream of gas 94 is held as if it were in a conduit by the purge gas in the secondary stream 96. The purge gas emerges from the purge gas inlet 74. The flow of purge gas into the view volume is widened by a purge baffle 75, causing the gas to then converge from the baffle toward the center of the view volume, namely to the clear zone 77 where the converging purge gas tends to coaxially pinch or constrain the primary stream of fluent material before entering the tip 81 of the outlet nozzle.

It will be noted that heaters 90 and 92 are mounted in collars 91 and 93, each collar having a portion surrounding a respective inlet nozzle 72 and an outlet nozzle 76. The inlet heater 90 and the outlet heater 92 are maintained at a temperature of 85°–90° C. to prevent condensation of vapor on the flow surfaces of the optics block.

Figure 10:
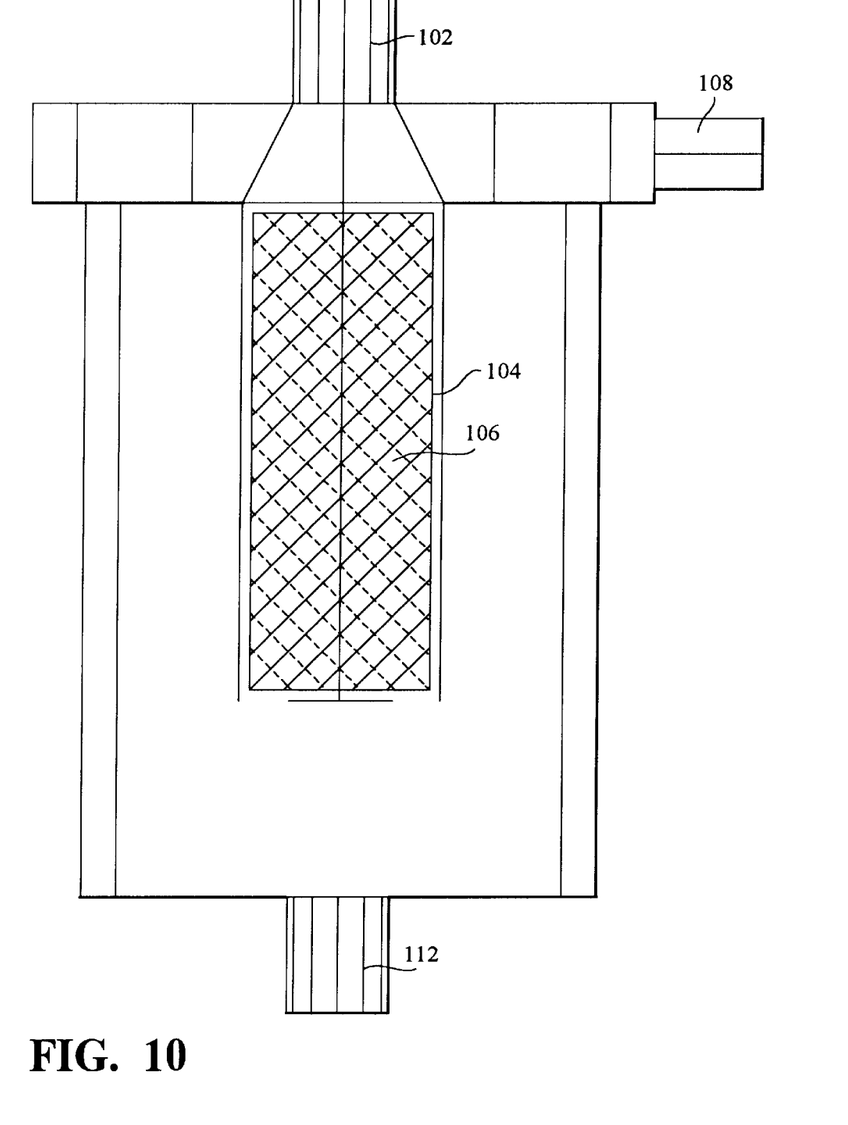
FIG. 10 is a sectional plan view of a filter in accordance with the plan illustrated in FIG. 6.

By the time gas exits outlet nozzle 76, there is good mixing of the primary and secondary fluent streams prior to passing into the filters. A typical one of the primary and secondary filters is shown in FIG. 10. A filter inlet conduit 102 receives the mixed primary and secondary streams of fluent material. Most of the stream flows into central filter chamber 104 and into filter medium 106. In the case of first filter 80 the filter media 106 is compressed foam with 0.05 mm size pores, although the pore dimension is not critical. The main consideration is to maintain good flow of gas through the filter inlet 102 into the filter where coalescence of the working fluid occurs and coalesced liquid flows into drain 112 by action of pumps, forcing liquid to be pulled from the filter and recycled to the reservoir of the saturator.

Since the pressure within the filter is constantly changing, some of the mixed primary and secondary streams of exhaust gas will pass through outlet port 108 to the next filter stage. This stage will have an identical construction as shown in FIG. 10, but the media may be different. For example, an absorptive material, such as activated charcoal may be used. Once again, the pump will pull coalesced liquid from the filter, although the filter will tend to get saturated over a period of time. Upon saturation, the filter medium should be changed.

In summary, a way has been found to stabilize a primary fluent stream carrying particles whose size has been enlarged by condensate traveling through the middle of the view volume. By surrounding the primary stream of fluent material with the secondary stream, both streams remain optically transparent to a beam of light, yet false counts and optical contamination are greatly reduced. At the same time, the working fluid condensed on the particles, is recirculated back toward the saturator so that the working fluid does not contaminate the ambient environment where the sampler is located, such as a production facility. The few particles that remain trapped in the working fluid and are returned to the reservoir are not a significant factor because they lack sufficient kinetic energy to cross the vapor liquid interface of the saturator and re-enter the sample flow. After an extended period of time, the working fluid should be changed and the reservoir cleaned.

We claim:

1. Apparatus for counting particles in a fluid stream comprising, an inlet nozzle with a central axis discharging a primary stream of fluent material from a saturator containing particles with a condensate of a working fluid thereon, an optically unobstructed view volume adjacent to the inlet nozzle for receiving the stream of fluent material, a light source directing a beam of light across the stream of fluent material within the view volume, the beam being modified by particles in the primary stream of fluent material, a photosensitive detector disposed to receive light associated with the modified beam, the detector producing electrical signals in response to the modified beam, indicative of particles therein, and an outlet nozzle with an axis common to the central axis of the inlet nozzle positioned adjacent to the view volume to receive and remove the stream of fluent material from the view volume, and a purge gas inlet introducing purge gas as a secondary stream of fluent material, surrounding the primary stream of fluent material, thereby providing a boundary layer of fluent material about the primary stream through the view volume, a secondary nozzle associated with the inlet nozzle discharging a secondary stream of fluent material coaxial with the primary stream into an outlet nozzle, a filter apparatus connected to receive said stream of fluent material from the outlet nozzle, the filter apparatus having a medium coalescing the working fluid toward a drain, and a conduit connecting said drain to the saturator, thereby recirculating the working fluid.

2. The apparatus of claim 1 wherein said purge gas inlet coaxially surrounds said inlet nozzle.

3. The apparatus of claim 1 wherein the detector is in light scattering detection relation relative to the light source.

4. The apparatus of claim 1 wherein said stream of fluent material contains particles having vapor condensed thereon.

5. The apparatus of claim 4 wherein said view volume is defined within a hollow block of solid material having a heater associated therewith maintained at a temperature discouraging accumulation of condensate thereon.

6. The apparatus of claim 1 wherein a working fluid is contained in a reservoir and vaporized therefrom, the vapor condensing on particles, forming said primary stream of fluent material.

7. The apparatus of claim 1 wherein said filter apparatus comprises first and second filters, the first filter having an overflow connection to the second filter whereby portions of the stream of fluent material not accommodated by the first filter flow to the second filter.

8. The apparatus of claim 7 where the media of the first and second filters are different.

9. The apparatus of claim 1 where the filter medium is foam.

10. The apparatus of claim 1 where the filter medium is activated charcoal.

11. Apparatus for counting particles in a fluid stream comprising, an inlet nozzle with a central axis discharging a primary stream of fluent material containing particles, an optically unobstructed view volume adjacent to the inlet nozzle for receiving the stream of fluent material, a light source directing a beam of light across the stream of fluent material within the view volume, the beam being modified by particles in the primary stream of fluent material, a photosensitive detector disposed to receive light associated with the modified beam, the detector producing electrical signals in response to the modified beam, indication of particles therein, an outlet nozzle with an axis common to the central axis of the inlet nozzle positioned adjacent to the view volume to receive and remove the stream of fluent material from the view volume, a purge gas inlet introducing purge gas as a secondary stream of fluent material, surrounding the primary stream of fluent material, thereby providing a boundary layer of fluent material about the primary stream through the view volume, a secondary nozzle associated with the inlet nozzle discharging a secondary stream of fluent material coaxial with the primary stream;

a working fluid contained in a reservoir and vaporized therefrom, the vapor condensing on particles, forming said primary stream of fluent material;

a first filter receiving a first portion of said secondary stream of fluent material discharged from the secondary nozzle, said first filter having a porous material therein through which said first portion of said secondary stream flows whereby vapor condensed on said particles now condenses in said foam;

a flow path extending between said first filter and said reservoir whereby condensate from the foam is returned to the reservoir via the flow path;

a second filter, in overflow relation to the first filter, receiving a second portion of said secondary stream of fluent material discharged from the secondary nozzle, said second filter having an absorptive material therein through which said second portion of said secondary stream flows whereby vapor condensed on said particles now condenses on said absorptive material; and a second flow path extending between said second filter and said reservoir whereby some condensate from the absorptive material is returned to the reservoir via the second flow path.

12. The apparatus of claim 11 wherein said purge gas inlet coaxially surrounds said inlet nozzle.

13. The apparatus of claim 11 wherein the detector is in light scattering detection relation relative to the light source.

14. The apparatus of claim 11 wherein said stream of fluent material contains particles having vapor condensed thereon.

15. The apparatus of claim 14 wherein said view volume is defined within a hollow block of solid material having a heater associated therewith maintained at a temperature discouraging accumulation of condensate thereon.

16. Apparatus for counting particles in a fluid stream comprising, a condensation nucleus counter including a saturator connected to an optics block defining a view volume with an inlet nozzle for a stream of fluent material having particles with condensate of a working fluid thereon and an outlet, a filter apparatus connected to receive said stream of fluent material from the outlet, the filter apparatus having a medium coalescing the working fluid toward a drain, and a conduit connecting said drain to the saturator, thereby recirculating the working fluid.

17. The apparatus of claim 16 wherein said filter apparatus comprises first and second filters, the first filter having an overflow connection to the second filter whereby portions of the stream of fluent material not accommodated by the first filter flow to the second filter.

18. The apparatus of claim 17 where the media of the first and second filters are different.

19. The apparatus of claim 16 where the filter medium is activated charcoal.

* * * * *